United States Patent
Pang et al.

(10) Patent No.: US 11,541,423 B2
(45) Date of Patent: Jan. 3, 2023

(54) ULTRASOUND TRANSDUCER WITH CURVED TRANSDUCER STACK

(71) Applicant: FUJIFILM Sonosite, Inc., Bothell, WA (US)

(72) Inventors: Guofeng Pang, Ajax (CA); Oleg Ivanytskyy, Toronto (CA); Robert Kolaja, Toronto (CA); Hossein Amini, Toronto (CA)

(73) Assignee: FUJIFILM Sonosite, Inc., Bothell, WA (US)

( * ) Notice: Subject to any disclaimer, the term of this patent is extended or adjusted under 35 U.S.C. 154(b) by 615 days.

(21) Appl. No.: 16/428,228

(22) Filed: May 31, 2019

(65) Prior Publication Data
US 2019/0366384 A1 Dec. 5, 2019

Related U.S. Application Data

(60) Provisional application No. 62/680,444, filed on Jun. 4, 2018.

(51) Int. Cl.
| | | |
|---|---|---|
| *B06B 1/06* | (2006.01) | |
| *A61B 8/00* | (2006.01) | |
| *G10K 11/30* | (2006.01) | |

(52) U.S. Cl.
CPC .......... *B06B 1/0622* (2013.01); *A61B 8/4488* (2013.01); *B06B 1/067* (2013.01); *B06B 1/0611* (2013.01); *G10K 11/30* (2013.01)

(58) Field of Classification Search
CPC ... A61B 8/4488; B06B 1/0622; B06B 1/0611; G10K 11/30
See application file for complete search history.

(56) References Cited

U.S. PATENT DOCUMENTS

| | | | | |
|---|---|---|---|---|
| 6,014,898 A | * | 1/2000 | Finsterwald | .......... B06B 1/0622 |
| | | | | 310/334 |
| 6,194,814 B1 | * | 2/2001 | Hanafy | ................ G10K 11/006 |
| | | | | 310/327 |
| 8,316,518 B2 | | 11/2012 | Lukacs et al. | |

(Continued)

FOREIGN PATENT DOCUMENTS

EP 0 641 606 B1 2/2000

OTHER PUBLICATIONS

International Search Report dated Sep. 24, 2019 in International Application No. PCT/US2019/034883.

*Primary Examiner* — J. San Martin
(74) *Attorney, Agent, or Firm* — Baker Botts L.L.P.

(57) ABSTRACT

A high frequency ultrasound array having a number of transducer elements that are formed in sheet of piezoelectric material. A frame having a coefficient of thermal expansion similar to that of the piezoelectric material surrounds the piezoelectric material and is separated from the piezoelectric material by an epoxy material. Kerf cuts that define the individual elements in the sheet of piezoelectric material extend across a full width of the sheet. In some embodiments, sub-dice kerf cuts that divide a single transducer element into two or more sub-elements also extend all the way across the width of the sheet. A lens positioned in front of the transducer elements can have a radius machined therein to focus ultrasound signals. The frame, transducer elements and lens are bent or curved with the desired radius to focus ultrasound signals.

19 Claims, 9 Drawing Sheets

(56) References Cited

U.S. PATENT DOCUMENTS

| | | | |
|---|---|---|---|
| 9,935,254 B2* | 4/2018 | Lukacs | H04R 31/00 |
| 2002/0007118 A1 | 1/2002 | Adachi et al. | |
| 2005/0272183 A1* | 12/2005 | Lukacs | B06B 1/0622 |
| | | | 438/109 |
| 2013/0049534 A1 | 2/2013 | Clark et al. | |
| 2016/0118572 A1 | 4/2016 | Lukacs et al. | |
| 2017/0143297 A1 | 5/2017 | Chaggares et al. | |
| 2017/0144192 A1 | 5/2017 | Chaggares et al. | |

* cited by examiner

ULTRASOUND TRANSDUCER WITH CURVED TRANSDUCER STACK

CROSS-REFERENCE TO RELATED APPLICATION(S)

The present application is related to, and claims the benefit of, U.S. Provisional Patent Application Ser. No. 62/680,444 filed Jun. 4, 2018, which is herein incorporated by reference in its entirety

TECHNICAL FIELD

The disclosed technology relates generally to phased array ultrasound transducers and in particular to high frequency, ultrasound transducers.

BACKGROUND

As will be appreciated by those skilled in the art, most modern ultrasound imaging systems work by creating acoustic signals from a number of individual transducer elements that are formed in a sheet of piezoelectric material. By applying a voltage pulse across an element, the element is physically deformed thereby causing a corresponding ultrasound signal to be generated. The signal travels into a region of interest where a portion of the signal is reflected back to the transducer as an echo signal. When an echo signal impinges upon a transducer element, the element is vibrated causing a corresponding voltage to be created that is detected as an electronic signal. Electronic signals from multiple transducer elements are combined and analyzed to determine characteristics of the combined signal such as its amplitude, frequency, phase shift, power and the like. The characteristics are quantified and converted into pixel data that is used to create an image of the region of interest.

A phased array transducer works by selectively exciting more than one element in the array at a time so that a summed wave front is directed in a desired direction. By carefully changing the phase (e.g. time delay) and in some cases, the amplitude of the signals produced by each transducer element, a combined beam can be directed over a range of angles in order to view areas other than those directly ahead of the transducer. For a phased array transducer to work well, the pitch of the individual transducer elements is generally required to be about ½ of the wavelength of the center frequency of the transducer or less. While low frequency, phased array transducers (e.g. 2-10 MHz) have been used for some time, high frequency phased array transducers have been difficult to manufacture due to the small size of the transducer elements and the higher attenuation of high frequency ultrasound signals.

High frequency ultrasound (e.g. 15 MHz and higher) is an increasingly used imaging modality that is used to image fine detail in a body and to capture images of moving tissues. As the operating frequency of a transducer increases, the size of the transducer elements decreases. However, many manufacturing techniques that are used to make lower frequency phased array transducers cannot simply be scaled to create high frequency phased array transducers. One component of the transducer that is expensive and time consuming to manufacture is a high frequency lens. A lens for a high frequency ultrasound transducer is typically a thin sheet of material that includes a concave radius to focus the ultrasound signals at a pre-determined depth. The radius is time consuming and expensive to put into the lens material. In addition, forming corresponding curvatures in any matching layers on the lens is a time consuming and expensive process. Given this problem, there is a need for improving the focusing mechanism of a high frequency ultrasound transducer array.

SUMMARY

The disclosed technology is a high frequency ultrasound transducer array having a frame that surrounds a sheet of piezoelectric material. The frame has coefficient of thermal expansion that is matched to the piezoelectric material. A number of transducer elements are formed in the sheet of piezoelectric material and one or more matching layers are coupled to a front face of the transducer elements in order to match an acoustic impedance of the transducer elements to an acoustic impedance of a lens that focuses the ultrasound signals produced. In one embodiment, kerf cuts are placed in the matching layers that align with the kerf cuts that define the individual transducer elements. The kerf cuts in the matching layers are filled with a material such as a loaded epoxy. A lens is secured to an outermost matching layer and also includes a number of filled kerf cuts that are aligned with the kerf cuts in the one or more matching layers. In one embodiment, one or more additional matching layers are added to a front surface of the lens to match an acoustic impedance of the lens material to the acoustic impedance of water.

In one embodiment, the transducer stack including frame, piezoelectric material and lens are bent to have a concave radius in order to focus ultrasound signals from the transducer elements. The transducer stack can be adhered to a curved support frame to hold the transducer stack in its curved configuration. In another embodiment, a curved bezel is secured to the transducer stack to maintain the curvature of the stack.

DETAILED DESCRIPTION

Figure 1:
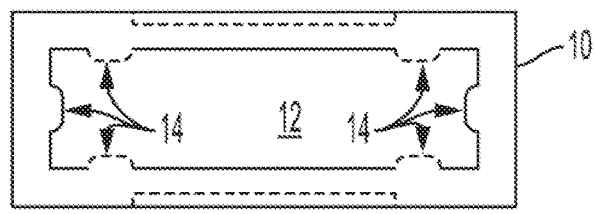
FIG. 1 is a top plan view of a frame that surrounds a piezoelectric sheet in accordance with an embodiment of the disclosed technology.

As will be described in detail below, a high frequency, ultrasound transducer includes a sheet of piezoelectric material that is surrounded by a frame. The frame is made from an electrically conductive or non-conductive material having a coefficient of thermal expansion (CTE) that is similar to the CTE of the sheet of piezoelectric material. The frame surrounds the piezoelectric material and is separated from the piezoelectric material by an insulating material such as an epoxy. Kerf cuts that define the individual transducer elements in the sheet of piezoelectric material extend across a full width of the piezoelectric sheet. In some embodiments, sub-dice kerf cuts divide a single transducer element into two or more sub-elements. In some embodiments, the sub-dice kerf cuts are parallel to the kerf cuts that define the individual transducer elements. In other embodiments, the sub-dice kerf cuts are cut at an angle or perpendicular to the transducer element kerf cuts to create a 1 3 composite. For example, 90 degree kerfs can be cut to create square or rectangular piezoelectric pillars in the piezoelectric sheet.

In previous generations of high frequency ultrasound transducers, a sheet of piezoelectric material was laser machined to create a number of kerf cuts that define individual transducer elements. The open space in the kerf cuts that define adjacent transducer elements and the sub-dice kerf cuts within an element were filled with an epoxy material before the sheet was lapped to a desired thickness. The kerf cuts had a length that was less than a width of the piezoelectric sheet so that a border or perimeter of the piezoelectric material provided some strength around the transducer elements.

While this approach works well, it is believed that improvements can be made. For example, the curing epoxy in the kerf cuts places the piezoelectric sheet under stress. Because the epoxy shrinks when it cures, each transducer element is pulled sideways into a kerf cut. While not significant for one or two elements, the stresses summed over all the elements may reach a level where the piezoelectric sheet can crack. In addition, it is believed that stresses caused by the shrinking the epoxy deform the transducer elements to create a constant stress bias on the transducer. Finally, because each transducer element is physically joined to the others at the perimeter of the sheet, there is some level of cross-talk between the elements as they are excited with a driving pulse and as the echo signals impinge upon the elements. As will be described below, one aspect of the disclosed technology is a transducer array design where the kerf cuts extend across an entire width of the piezoelectric sheet. Preliminary simulations indicate that the disclosed design not only reduces the stresses caused by the curing of the kerf filling material but also reduces coupling between the transducer elements. This is supported by experimentation showing a significant improvement in bandwidth and sensitivity over the previous kerf designs that extend for less than the full width of a piezoelectric sheet.

As will be appreciated by those skilled in the art, the embodiments shown in the Figures are drawn for the purpose of explaining how to make and use the disclosed technology and are not necessarily drawn to scale.

As shown in FIG. 1, a transducer stack includes a frame 10 into which a sheet of piezoelectric material is placed. The frame 10 has a central opening 12 that receives the sheet of piezoelectric material and creates a space between an outer edge of the piezoelectric sheet and an interior edge of the frame 10. The frame 10 is preferably made of a material having a coefficient of thermal expansion (CTE) that is similar to the CTE of the piezoelectric material. In some embodiments, the sheet of piezoelectric material is made from lead zirconate titanate, more commonly known as PZT. For the remainder of the description, the piezoelectric material is described as PZT. However, it will be appreciated that other materials such as single crystal ferroelectric relaxors (e.g. PMN-PT) or synthetic piezoelectric materials could be substituted for PZT. In the case of PZT, one suitable choice for the frame material is alumina, which is a non-conductive ceramic with a CTE that is close to the CTE of PZT. Alumina has a CTE of about 7.2 microns/M° C. where the CTE for PZT is approximately 4.7 microns/M° C. However, it will be appreciated that other materials with a coefficient of thermal expansion similar to that of the piezoelectric material could be used such as molybdenum or fine grain isotropic graphite. For the purposes of the present application, coefficients of thermal expansion are similar if the piezoelectric material in the frame doesn't crack due to thermal stresses when operated and handled over its normal temperature operating range. In some embodiments, the frame 10 may include a number of inwardly extending tabs or fiducials 14 (shown in dashes) that center the PZT in the opening and space the PZT from the inside edge of the frame. In some embodiments, the tabs 14 are used if the frame 10 is made of a conductive material like molybdenum or graphite but are not used if the frame 10 is made of non-conductive alumina.

Figures 2A, 2B:
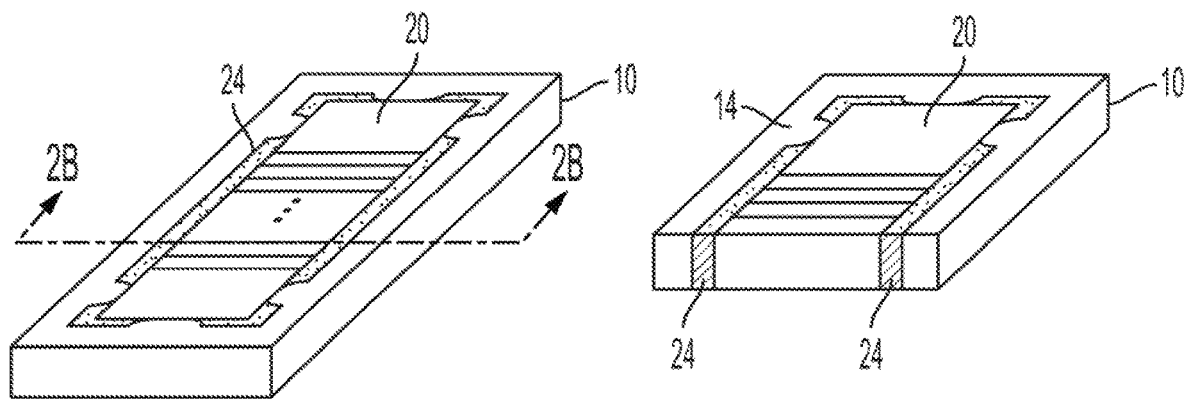
FIG. 2A is an isometric view of a frame surrounding a piezoelectric sheet and that is filled with an epoxy material in accordance with an embodiment of the disclosed technology.
FIG. 2B an isometric, cross-sectional view of the frame and piezoelectric sheet shown in FIG. 2A.

FIGS. 2A and 2B show a sheet of piezoelectric material 20 placed in the opening 12 of the frame 10. The space between the interior edge of the frame 10 and outer edges of the sheet of piezoelectric material 20 is filled an insulating filling material 24. In one embodiment, the filling material 24 is an epoxy such as from the EPO-TEK 301 family available from Epoxy Technology, Inc, Billerica Mass. that is doped with hafnium oxide or ceramic particles. The particles are added to the epoxy to resist shrinkage and to resist laser machining as described below. In the embodiment shown in FIG. 3, the filling material 24 is molded around the sides of the sheet of piezoelectric material 20 and is flush with a top surface of the sheet piezoelectric material 20 to form a stack 30 having a top surface 32 and a bottom surface 34. In the description below, the bottom surface 34 of the stack faces towards the region of interest and the top surface 32 faces proximally toward the ultrasound operator in a finished transducer.

Once the filling material 24 is cured, the top surface 32 and the bottom surface 34 of the stack 30 are lapped, ground or otherwise made flat to remove any extra epoxy and to provide flat references for a number of additional machining steps as will be described.

Figure 3:
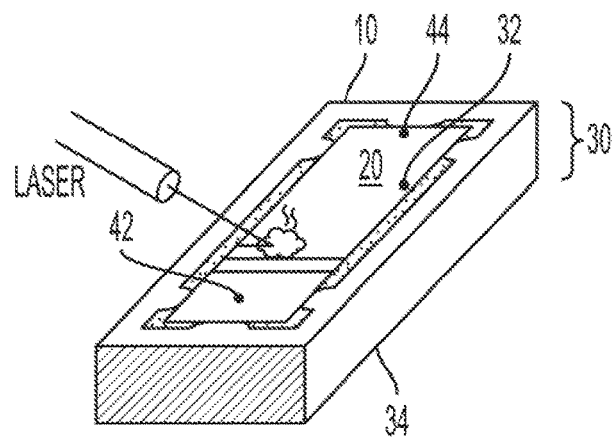
FIG. 3 illustrates how transducer element kerf cuts and sub-dice kerf cuts are fashioned in the piezoelectric sheet with a laser in accordance with an embodiment of the disclosed technology.

With the top and bottom surfaces lapped, kerf cuts are created in the PZT sheet 20 with an excimer or other patterning laser. As shown in FIG. 3, kerf cuts 40 are cut across the entire width of the PZT sheet 20 from one edge to the other. If the frame 10 includes the alignment tabs or fiducials 14, the kerf cuts begin at positions away from each end of the PZT sheet to define inactive regions 42 and 44 that are located near the alignment tabs 14. In this way, the ends of the transducer elements are separated from the interior edge of the frame 10 by an epoxy filled gap. If the alignment tabs 14 are not used, then the entire PZT sheet can be diced to form transducer elements. Because the epoxy of the filling material 24 is softer than the PZT, the transducer elements are effectively floating in the cured filling material 24. As indicated above, the kerf cuts that define individual transducer elements can begin in the filling material on one side of the frame and continue across the entire width of the PZT sheet 20 to the filling material 24 on the other side of the PZT sheet.

In one embodiment, the kerf cuts are placed at a desired pitch and to a depth sufficient to form the transducer elements depending on the desired center frequency of the transducer being manufactured. In some embodiments, a transducer element comprises two electrically connected sub-elements that are separated by a sub-dice kerf cut that extends across the entire width of the PZT. In one embodiment, the sub-dice kerf cuts have the same depth as the kerf cuts that define individual transducer elements. However, the sub-dice kerf cuts could be cut to a shallower depth than the primary kerfs such that they do not extend all the way through the final thickness of the PZT. In other embodiments, the transducer elements may not include any sub-dice kerf cuts.

Figure 4:
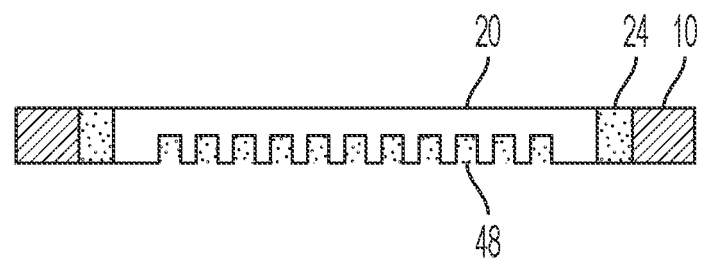
FIG. 4 is an enlarged, cross-sectional view of a piezoelectric sheet showing a filler epoxy placed in the transducer element kerf cuts and the sub-dice kerf cuts.

After the kerf cuts that define the transducer elements and the sub-dice elements (if used) are fashioned by the laser, the kerf cuts are filled with an epoxy material 48 as shown in FIG. 4. In one embodiment, the epoxy material used to fill in the kerf cuts is a doped flexible EPO-TEK 301 epoxy.

In one embodiment, the epoxy material 48 is applied to the part under vacuum so that no air is trapped in the bottom of the kerfs cuts. A liquid epoxy is applied and the part is then put under relatively high pressure (e.g. 100+ psi) to drive the liquid epoxy into the kerf cuts and allowed to cure.

After the epoxy 48 in the kerf cuts has cured, the bottom surface 34 of the stack is lapped, ground or otherwise made flat. Next, a grounding layer 60 of a conductive metal such as gold or gold+ an adhering metal such as chromium is applied to the front face of the stack by sputtering or a similar technique. The conductive grounding layer 60 covers a front face of the diced PZT, a front face of the frame 10 and a front face of the epoxy filling material 24 that lies between the frame 10 and the edge the PZT sheet (as viewed when the transducer is in use).

Figure 5:
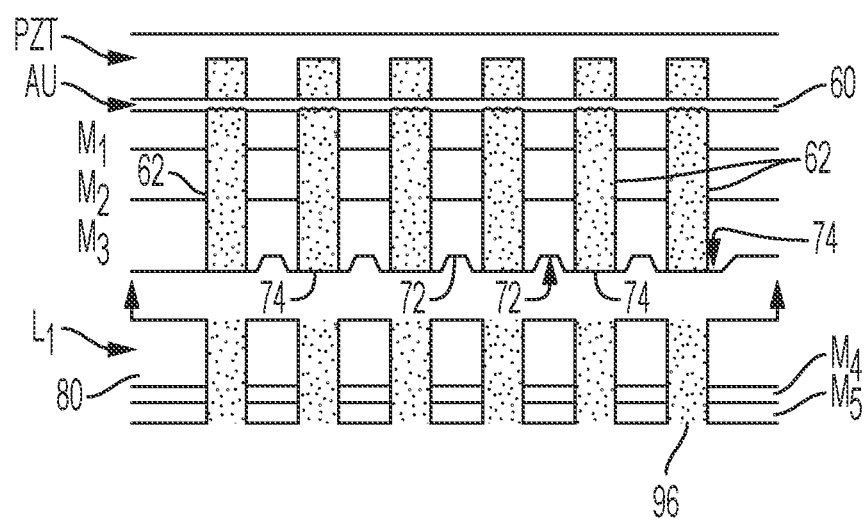
FIG. 5 is an enlarged, cross-sectional view of a portion of a transducer stack showing a number of matching layers applied to a front face of a transducer layer that are diced and filled with an epoxy material and a lens that is bonded to the matching layers in accordance with an embodiment of the disclosed technology.

After the conductive grounding layer 60 is applied, one or more matching layers M1, M2 and M3 (in the embodiment shown) and a lens L1 are applied to the front surface of the stack as shown in FIG. 5. The number of matching layers used depends on the mismatch between the acoustic impedance of the PZT and the acoustic impedance of the lens material. In the illustrated embodiment, three matching layers M1, M2 and M3 are used on the front surface of the stack. In one embodiment, each of the matching layers comprises an epoxy material that is doped with powders to alter its acoustic performance in order to achieve a required transducer performance.

In one embodiment, matching layer M1 that is applied over the conductive ground layer 60 comprises a layer of EPO-TEK 301 epoxy doped with tungsten powder.

In one embodiment, matching layer M2 is applied over the surface of matching layer M1 and comprises a layer of EPO-TEK 301 epoxy doped with tungsten powder and silicon carbide (SiC) nanoparticles.

In one embodiment, matching layer M3 is applied over the surface of matching layer M2 and comprises a layer of EPO-TEK 301 epoxy doped with silicon carbide (SiC) nanoparticles.

In one embodiment, each of the matching layers has a thickness that is preferably an odd multiple of a ¼ wavelength at the center operating frequency of the transducer. Most often, the thicknesses will be one of 1, 3, 5 or 7 quarter wavelengths thick. However, this may vary depending on the desired acoustic properties of the transducer. It will be appreciated that these matching layers are merely exemplary and that other matching layer compositions may be used depending on the desired operating frequency of the transducer, the lens material to be used etc. The details of how matching layers can be doped with particles to achieve a desired acoustic impedance are considered to be known to those of ordinary skill in the art of ultrasound transducer design.

After each matching layer is applied and cured, the front face of the stack is lapped to achieve a desired thickness and to keep the front surface flat. In some embodiments, kerf cuts 62 are cut in the cured matching layers with a laser to align with both the kerf cuts that define the individual transducer elements and the sub-dicing kerf cuts (if used). In other embodiments, kerf cuts 62 can be made in the matching layers to align with only the kerf cuts that define the individual transducer elements and not over the sub-dice kerf cuts. In one embodiment, the kerf cuts 62 extend through the matching layers M3-M1 and may extend partially or fully through the grounding layer 60 with no loss of connectivity between the grounding layer and the transducer elements. Once created, the kerf cuts 62 in the matching layers are filled with the same filled epoxy material that fills the kerf cuts in the PZT material.

Figure 6A:
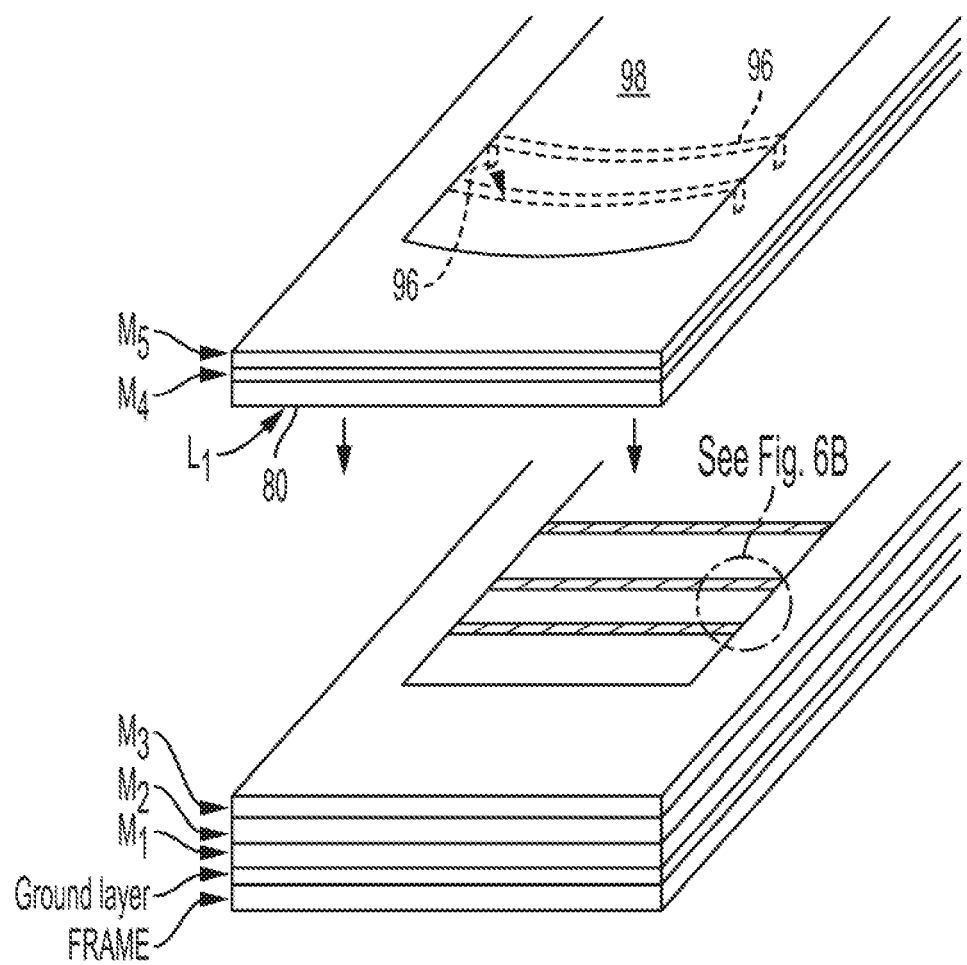
FIG. 6A is a partial isometric view of a lens and matching layers placed over the transducer stack.

After the matching layers are kerf cut, the lens material is bonded to the matching layers. In a high frequency phased-array, kerf cuts 96 are formed in the lens 80 that are aligned with the kerf cuts 62 in the matching layers (including matching layers M4 and M5 disposed on the front of the lens) as shown in FIG. 6A. In some embodiments, the lens 80 includes kerf cuts 96 that are aligned with both the transducer element kerf cuts and the sub-dice kerf cuts. In other embodiments, the lens only includes kerf cuts that are aligned with the kerf cuts that define the individual transducer elements. In some embodiments, kerf cuts are made in the lens material and filled with a doped epoxy prior to mounting the lens to the matching layers. In other embodiments, the lens can be bonded first and then kerf cut and filled. A curvature 98 is machined into the front side of the lens so that the lens focuses the ultrasound in a plane at a desired depth.

Figure 6B:
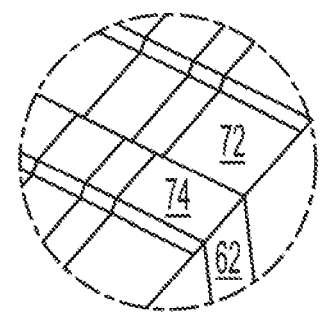
FIG. 6B is a close-up view of a number of ridges formed in a top matching layer that support a lens in accordance with some embodiments of the disclosed technology.

In some embodiments, depressions or indentations 72 are laser machined into the uppermost matching layer (e.g. M3) at positions between the filled kerf cuts 62 thereby forming a number of beams or ridges 74 at the top of the filled kerfs that extend across the width of the PZT sheet as best shown in FIG. 6B. The beams 74 support the lens 80 across the width of the PZT sheet. It is believed that the beams 74 help maintain a consistent distance between the rear surface of the lens 80 and the uppermost matching layer as the lens is being secured to the stack whereas without the beams/ridges the distance between a center area and the uppermost matching layer may vary as the two are being secured together if the lens 80 is only supported around a perimeter of the lens. In high frequency arrays where the tolerances are very tight, having the beams/ridges 74 may help ensure a consistent lens-to-transducer distance over the entire area of the active elements. If the uppermost matching layer does not include filled kerf cuts, the ridges 74 can be formed anywhere in the matching layer and not between the filled kerf cuts in the lower matching layers.

In one embodiment, the same material used for the uppermost matching layer M3 is used to glue the lens 80 to the stack. Because the indentations 72 are shallow and the same material used for the uppermost matching layer M3 is used as a glue to secure the lens 80 to the matching layer, there is minimal acoustic discontinuity at the bond line.

For a transducer to operate well as a phased-array, the beam pattern of the energy produced by each element at the front face of the lens has to be sufficiently wide so that the lateral components can combine with the lateral components of the beams from adjacent elements to effectively steer the beam. In one embodiment, the beam patterns have energy at +/−45 degrees from normal that exceeds −6 dB in signal power.

For low frequency transducers, lens materials are available that allow such transducers to be made. However, at high frequencies, the physical properties of such materials make them unacceptable for transducer designs, For example, silicone materials are often used as a lens material for low frequency transducers due to their close acoustic impedance to water. However, the absorption of ultrasound in silicone increases exponentially with frequency and at 15 MHz+, the absorption in the material is too great to allow it to be used as an effective lens. To overcome such absorption, harder materials are often used for high frequency ultrasound lenses such as polymethylpentene (sold under the tradename TPX) and cross-linked polystyrene (sold under the tradename Rexolite). While acceptable for non-phased arrays, such materials are difficult to use in phased arrays because of Snell's law.

With Snell's law, energy passing from a faster material to a slower material tends to bend towards a line normal to the interface. This is precisely the wrong direction for a phased array when it is desired that a portion of the beam energy extend at an angle away from normal. To compensate for the Snell's law effect, energy has to be supplied at a greater angle of incidence that quickly approaches a critical angle of the lens material where all the energy is reflected internally. In an ultrasound transducer, internally reflected energy from one transducer element can cause spurious signals to be generated at neighboring elements. In addition, phase aberrations associated with such internal reflections make it nearly impossible to perform beamforming with signals from multiple adjacent transducer elements.

To solve these problems, a phased array transducer design in accordance with the disclosed technology includes a lens configured so that it has an anisotropic speed of sound in the forward direction compared to a sideways or lateral direction in the lens. In one embodiment, a lens is made from a material having a speed of sound that is much faster than the speed of sound in the material that fills the kerf cuts in the lens. As shown in FIG. 6A, a lens 80 includes a sheet of polybenzimidazole (sold under the tradename Celazole™). The lens (and outer matching layers if used) is patterned with a laser to form a number of kerf cuts 96 that can align with the kerf cuts defining individual transducer element or the kerf cuts defining individual transducer elements and the sub-dice kerf cuts. Celazole is useful as a high frequency lens material because it has a high speed of sound, and because it can withstand the heat of the laser used when making the kerf cuts at a fine pitch (e.g. at 40 um or less for a 20+ MHz phased array) without melting. In addition, Celazole can be bonded to the epoxy of the uppermost matching layer of the transducer stack directly so that no cyanoacrylate (CA) layer of glue is necessary.

In one embodiment, the kerf cuts 96 in the lens 80 and outermost matching layers are filled with a material having a much slower speed of sound than the speed of sound of the lens material such as a powder filled or doped epoxy or RTV 60 silicone.

In some embodiments, the lens 80 also includes one or more matching layers M4 and M5 on its front surface that match the impedance of the lens material to water. M4 and M5 are formed to have a curvature that matches and is aligned with the curvature of the lens. In some embodiments, two powder-filled or doped epoxy matching layers (M4, M5) are applied to the front surface of the lens. In one embodiment, the matching layers on the lens are applied on mandrel having the same radius of curvature as the radius or curvature that is machined into the lens material. In some embodiments, the outer matching layers M4, M5 are diced with the laser to continue the kerf cuts 96 formed in the lens material 80 and filled with the same material that fills the kerf cuts in the lens material. In other embodiments, the matching layers on the front of the lens 80 may omit the kerf cuts on one or both of M4 and M5.

With this construction, the lens material between the kerf cuts 96 in the lens 80 forms a number of mini-waveguides that channel the energy of the ultrasound transducer elements in a direction straight ahead with less energy spreading laterally in the lens. In one embodiment, the speed of sound through the lens in the axial direction of the transducer stack is greater than the speed of sound in a direction sideways through the lens or in a direction parallel to a front face of the lens.

Figure 7:
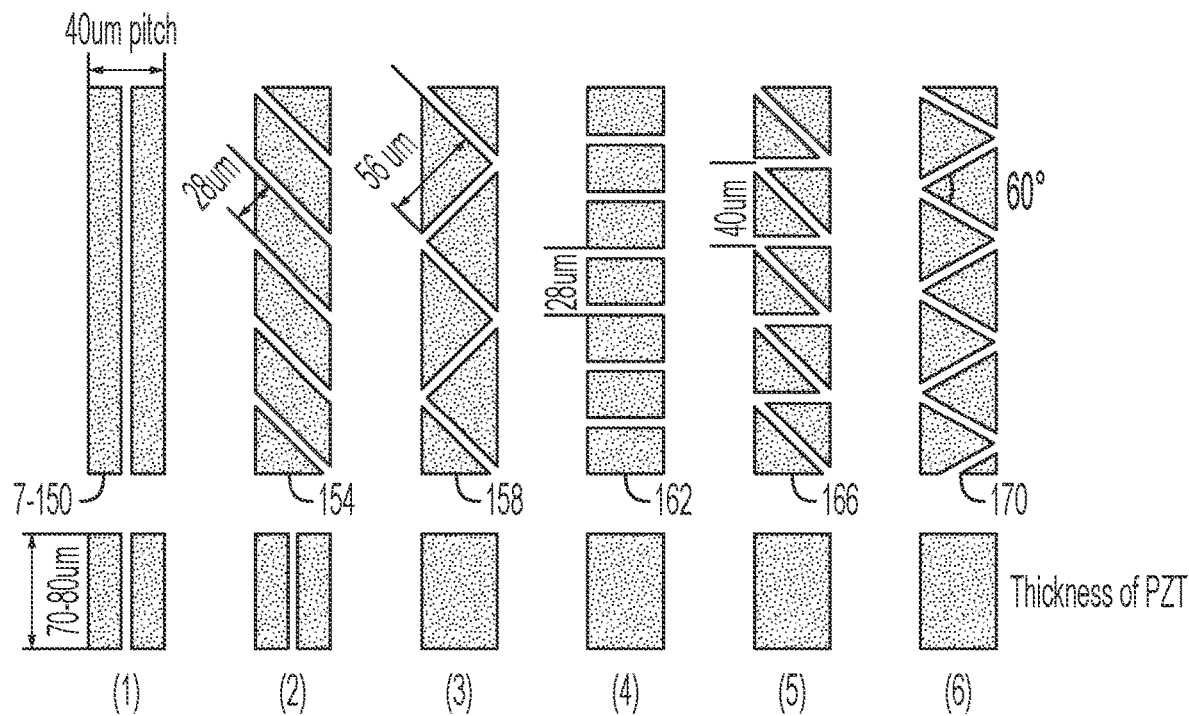
FIG. 7 shows a number of alternative sub-dice kerf cut patterns for a piezoelectric layer in accordance with embodiments of the disclosed technology.

In some embodiments, additional kerf cuts can be machined into the PZT layer in addition to those defining the individual transducer elements. FIG. 7 illustrates a number of possible sub-dicing patterns. A pattern 7-150 is a conventional sub-dice pattern where a transducer element is divided lengthwise down its center by a single sub-dice kerf cut. This sub-dice kerf cut has the same length as the transducer element. As will be appreciated by those skilled in the art, the width/height ratio of a transducer element should be less than or equal to the "golden ratio" of about 0.6 to minimize lateral vibrational modes in the PZT. In some embodiments of the disclosed technology, an excimer UV laser can cut a kerf line of approximately 6 um in width. At a 40 micron element pitch and 70-80 micron PZT thickness, this ratio can be met without using a center sub-dice kerf.

Other sub-dice patterns may be useful for certain transducer applications. A pattern 154 includes a number of parallel sub-dice kerf cuts that are cut at an acute angle (e.g. 55 degrees) with respect to the kerf cuts that define the transducer elements. In the embodiment shown, the parallel sub-dice kerf cuts are spaced 28 microns apart but other spacings could be used.

A third sub-dice pattern 158 is formed by alternating sets of parallel cuts that are acute with respect to the direction of the kerf cuts that define the transducer elements. The result is a set of alternately oriented, triangular PZT pillars each having a base that is aligned with a kerf cut defining the transducer element and a height that is the width of the transducer element. In the embodiment shown, each such triangle has a base that is 56 microns wide and a height of 40 microns for a transducer with elements at a 40 micron pitch.

A fourth pattern 162 is made with sub-dice kerfs cuts that are perpendicular to the kerf cuts that define the transducer elements. In this pattern, a number of rectangular PZT pillars are formed with a height of, for example, 28 microns and width equal to the width of the transducer elements (40 microns in the embodiment shown).

A fifth pattern 166 is made with sub-dice kerf cuts that are formed by a plurality of parallel cut kerf cuts oriented at an acute angle (e.g. 45 degrees) with respect to the kerf cuts defining the individual transducer elements and that are interspaced with kerf cuts that are perpendicular to the kerf cuts that define the individual transducer elements. This pattern forms a number of alternating right triangles with their hypotenuses facing each other in the transducer element. In the embodiment shown, the legs of the right triangles are 40 microns long.

A sixth pattern 170 of kerf cuts forms a number of alternately oriented equilateral triangles in the transducer element by forming kerf cuts at 60 degrees with respect to the kerf cuts that define the individual transducer elements.

Figure 8:
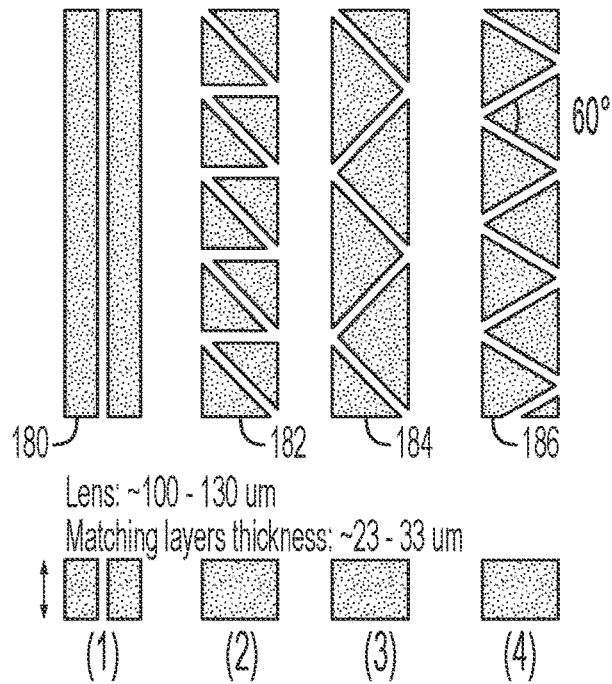
FIG. 8 shows a number of alternative sub-dice kerf cut patterns for a number of matching layers in accordance with embodiments of the disclosed technology.

FIG. 8 shows a number of possible sub-dice kerf cuts that can be formed in the matching layers (M1-M5) to correspond to the sub-dice kerf cuts in the PZT layer.

A pattern 180 corresponds to the pattern 7-150 with a single kerf cut defining a pair of sub-diced elements. A pattern 182 corresponds to the right triangular pattern 166. A pattern 184 corresponds to the alternating triangular pattern 158, while a pattern 186 corresponds to the alternating equilateral triangle pattern 170.

As indicated above, in some cases the matching layers include kerf cuts that match the sub-dice kerf cuts in the PZT layer. In other embodiments, the matching layers include fewer than all the sub-dice kerf cuts in the PZT layer and may only include kerf cuts matching the kerf cuts that define the individual transducer elements.

Figure 9:
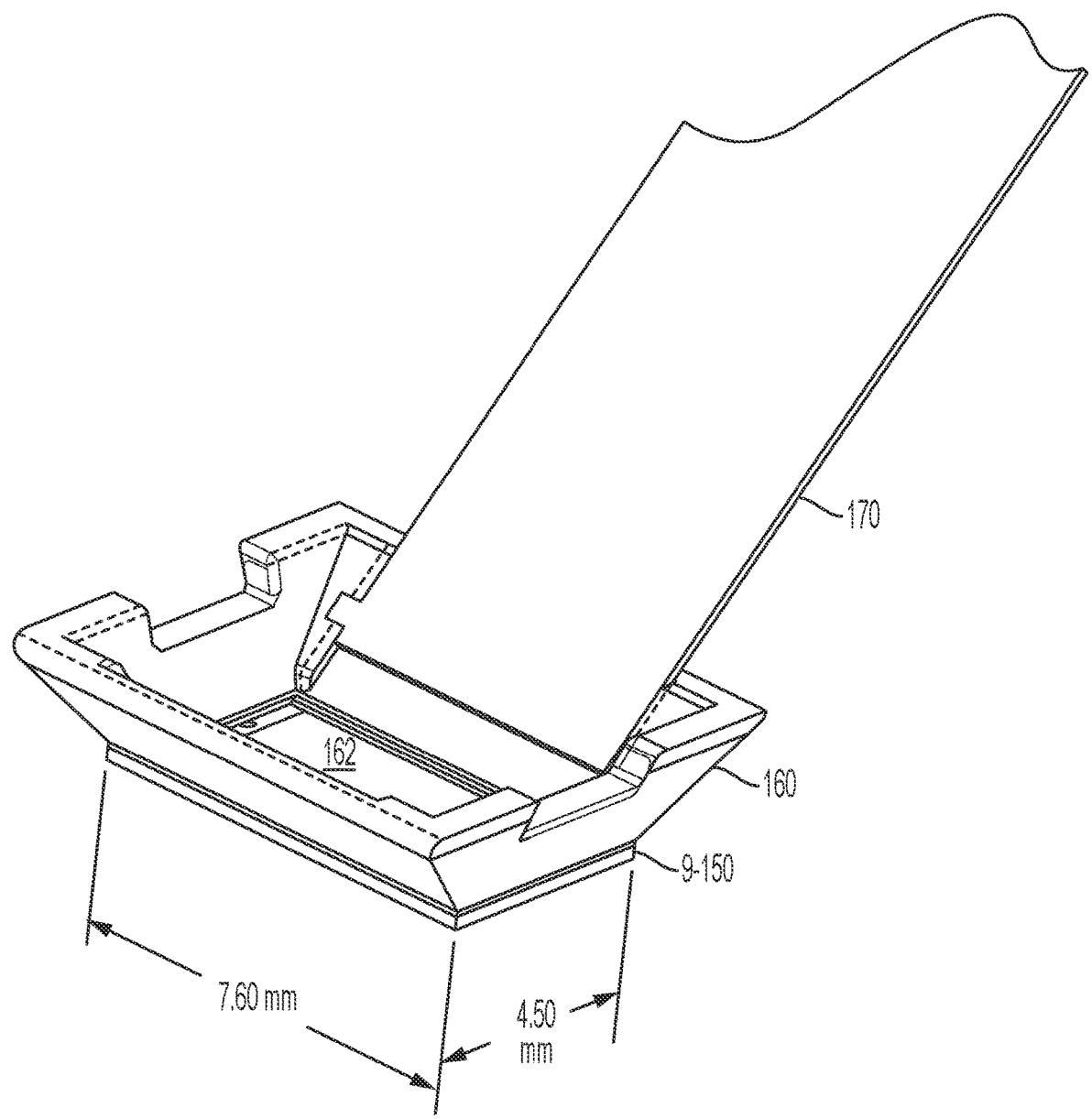
FIG. 9 shows a conductive support frame secured to a transducer stack in accordance with an embodiment of the disclosed technology.

As indicated above, with the lens 80 bonded to the transducer stack, the rear or proximal side of the transducer stack can be manufactured. First the PZT layer and frame are lapped to a desired thickness depending on the desired operating frequency of the transducer. Then, as best shown in FIG. 9, a conductive support frame 160 is secured with a conductive epoxy adhesive to the rear or proximal side of the transducer stack 9-150. The frame 160 is preferably conductive and is made of a metal having a CTE that is similar to the PZT such as molybdenum. In the example shown, the transducer stack 9-150 has an elevation dimension of 4.5 mm and an azimuthal or width dimension of 7.6 mm. The support frame has an open area 162 through which the rear surface of the individual exposed PZT transducer elements are accessible.

The support frame 160 supports one or more flexible circuits 170 having traces (not shown) that deliver electrical signals to and from the transducer elements. In one embodiment, a first flexible circuit has traces connected to all the even numbered transducer elements and a second flexible circuit on opposite side of the frame 160 (not shown) has traces connected to all the odd numbered transducer elements. In some embodiments, a single flexible circuit includes traces for both the even and odd transducer elements.

Figure 10:
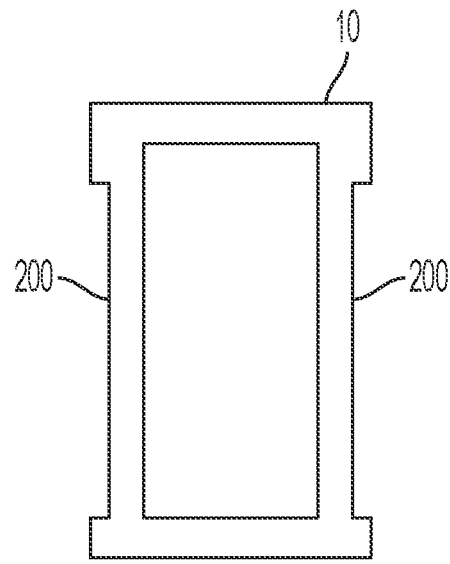
FIG. 10 shows an alternative embodiment of a frame that surrounds a piezoelectric sheet in accordance with the disclosed technology.

A ground plane in the flex circuit (not shown) is electrically connected to the conductive support frame 160 on the back side of the transducer with a conductive epoxy or the like. The support frame 160 therefore acts as part of a conductive path between the common ground electrode on the front side of the transducer stack and the ground plane in the flex circuits. If the frame surrounding the PZT sheet is conductive (e.g. graphite or molybdenum) then the frame itself becomes part of the conductive path. If the frame is non-conductive (e.g. alumina) then a conductive path is included between the frame and the common ground electrode on the front of the transducer stack. FIG. 10 shows an embodiment of a frame 10 having a pair of cut outs 200 along its long dimension that can be filled with a conductive epoxy to form a conductor between the front of the frame and the rear of the frame that in turn connects to the conductive support frame 160. Other mechanisms for providing the conductive path could include vias or conductive foils, wires or the like that connect the common ground electrode on the front of the PZT elements and the conductive support frame 160 or the ground electrodes in the flex circuits.

Once the conductive support frame 160 is secured to the transducer stack, electrical pathways are then made between exposed portions of the traces in the flex circuits and the individual transducer elements.

In one embodiment, conductive pathways are formed on the proximal side of the transducer elements to allow traces in flexible connectors 170 (e.g. flex circuits) to be electrically connected to the transducer elements. In some embodiments, the pathways are created by filling the frame with a particle filled epoxy, creating channels in the epoxy from a transducer element to a corresponding trace in the flex circuit with a laser and by plating the channels with gold or gold plus chromium followed by removing the gold in areas where it is not wanted and cleaning up the paths with the laser. Descriptions of suitable patterning processes used to create the conductive paths between the transducer elements and the traces in the flex circuits in accordance with some embodiments of the disclosed technology are found in commonly owned U.S. Patent Publication No. 2017-0144192 A1 and U.S. Pat. No. 8,316,518, which are herein incorporated by reference in their entireties.

Figure 11:
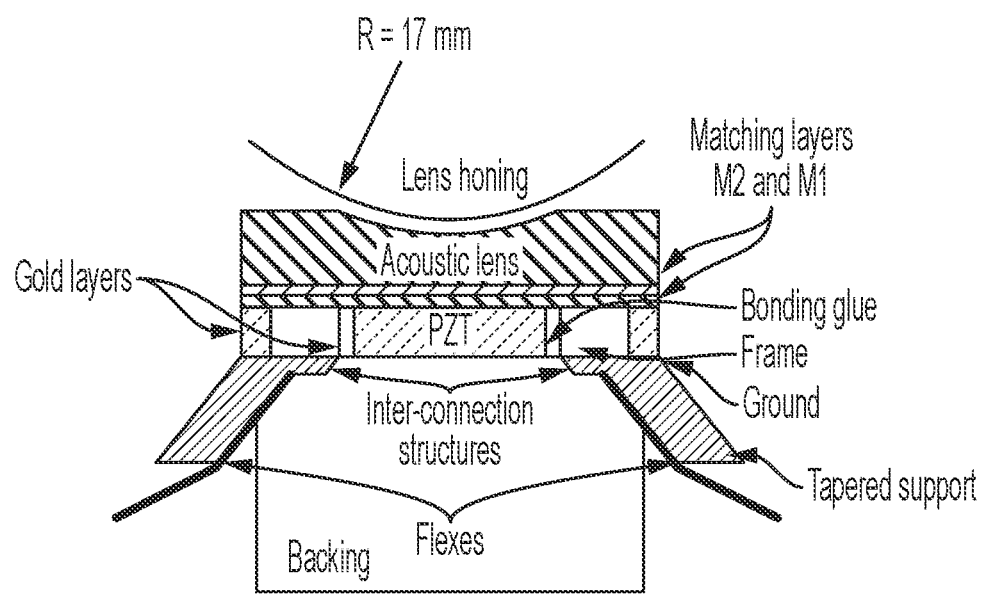
FIGS. 11 and 12 are cross-sectional views of a high frequency phased array transducer in accordance with an embodiment of the disclosed.
Figure 12:
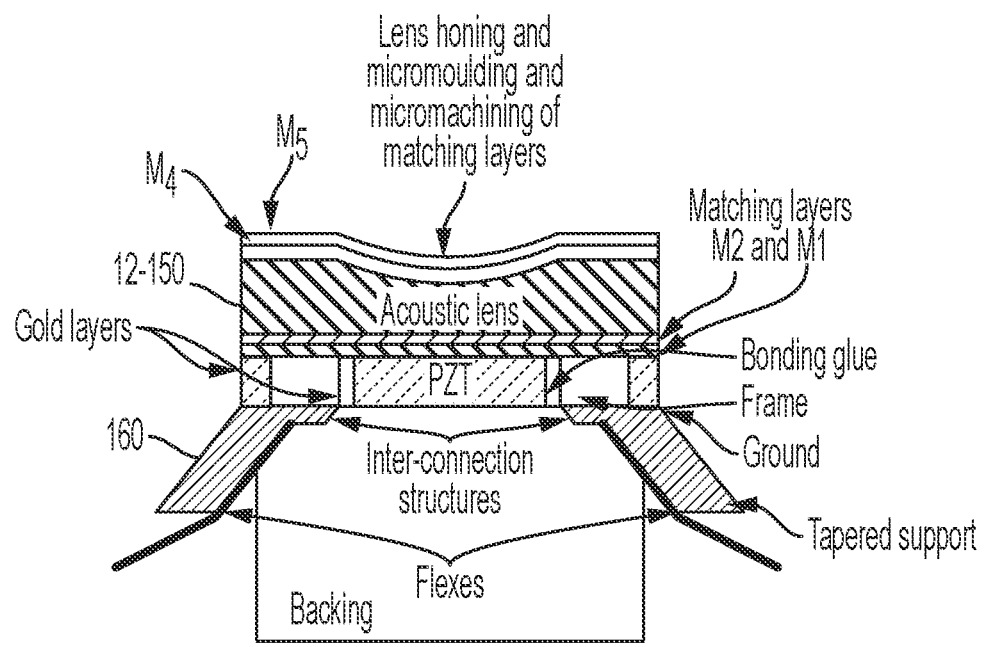

Once the connections have been made between the transducer elements and the traces in the flex circuits, a backing layer (not shown) is secured to the assembly behind the transducer elements. FIGS. 11 and 12 are cross-sectional views of a transducer assembly showing a transducer stack with a PZT layer, a tapered support frame surrounding the PZT layer and a lens 12-150 coupled to the stack through a number of matching layers. In the embodiment shown, the lens 12-150 has a radius of curvature of 17 mm that is machined into the lens material before the lens matching layers are applied. Two matching layers (M4, M5) are applied to the front surface of the lens. In one embodiment, the matching layers on the lens are applied on mandrel having the same radius of curvature as the radius that is machined into the lens material. The tapered support frame supports the flex circuits that provide signals to and receive signals from the transducer elements.

Although the disclosed embodiments show element spacings that are suitable for a high frequency phased array, it will be appreciated that the structure of the transducer including a piezoelectric sheet, surrounding frame, matching layers and lens could be used for non-phased array transducers or lower frequency transducers. In addition, if used at lower frequencies, then other lens materials such as TPX or Rexolite could be used.

Figure 13:
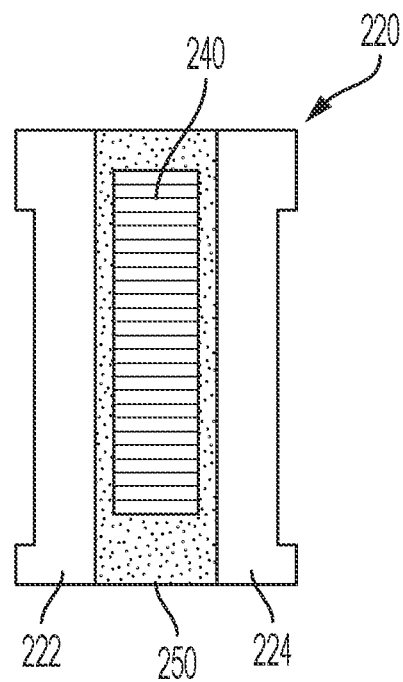
FIG. 13 shows an alternative embodiment of a frame that surrounds a piezoelectric sheet that allows the transducer stack to be curved in accordance with another embodiment of the disclosed technology.

In some embodiments, the step of forming a radius in the front face of the lens material to set its focal distance can be fully or partially avoided by bending the transducer stack to have a desired a radius in the elevation direction. FIG. 13 shows one embodiment of a flexible frame 220 that can surround a piezoelectric sheet 240 in a manner that allows the transducer stack to be curved after assembly. In this embodiment, the frame 220 includes a pair of side rails 222, 224 made of alumina or other material with a CTE that is similar to that of PZT (e.g. molybdenum, graphite). The side rails 222, 224 may include tabs or fiducials (not shown) that space a PZT sheet 240 from an inner edge of the side rails if the side rails are conductive. In embodiment, the side rails do not extend around the complete perimeter of the piezoelectric sheet but are open on two opposing sides to allow a flexible adhesive 250 such as an epoxy to fill the gap between the frame 220 and the PZT sheet 240. If the frame is made of a metal (e.g. molybdenum) that can be bent, then the frame may extend around the entire perimeter of the piezoelectric sheet. In this embodiment, the transducer stack is built by laser machining the PZT to form the transducer elements and sub-dice elements (if used), adding the grounding electrode and the one or more matching layers and the lens as described above.

Figure 14:
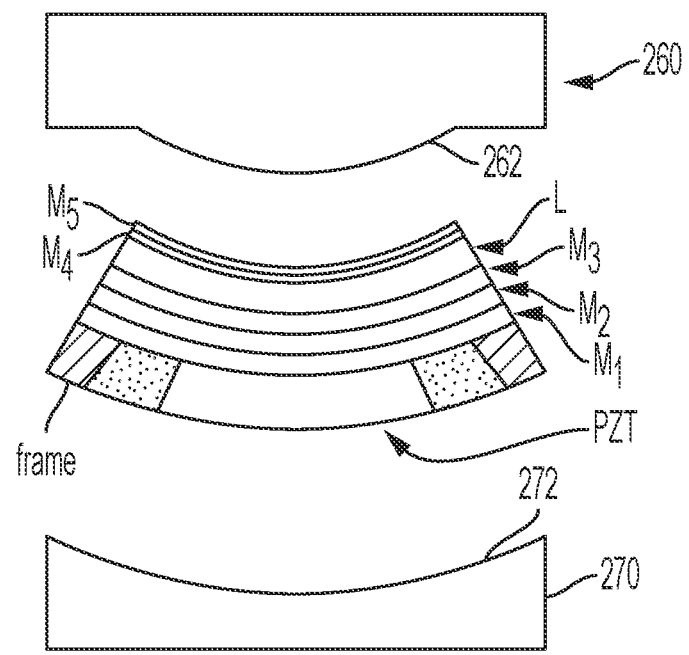
FIG. 14 is a cross-sectional view of a mold that can be used to bend a transducer stack in accordance with an embodiment of the disclosed technology.

Once the transducer stack is formed, it can be curved to have a desired radius by pressing the stack between elements of an appropriately shaped mold 260 as shown in FIG. 14. In this embodiment, the mold has one section 262 with a convex-shaped curvature and a second section 270 with a correspondingly shaped concave curvature 272. The transducer stack can be pressed between the two sections of the mold while under heat to soften the epoxies and bend the transducer stack to have the corresponding shape. If the PZT layer is thin (such as, but not limited to 80 microns or less), the transducer elements of the PZT layer will bend without cracking. Once cooled, the two sections 262, 270 of the mold are removed and the transducer stack will retain the desired curvature in the elevation direction of the lens to focus the ultrasound signals at the desired distance.

In the embodiment shown, the transducer stack is only bent in the elevation direction. However, it will be appreciated that the stack could also be bent to have a compound concave curve one or both of the elevation and azimuthal directions. Similarly, in some embodiments, it may be desirable to put a convex curve into the transducer stack in one or both of the elevation or azimuthal directions.

Figure 15:
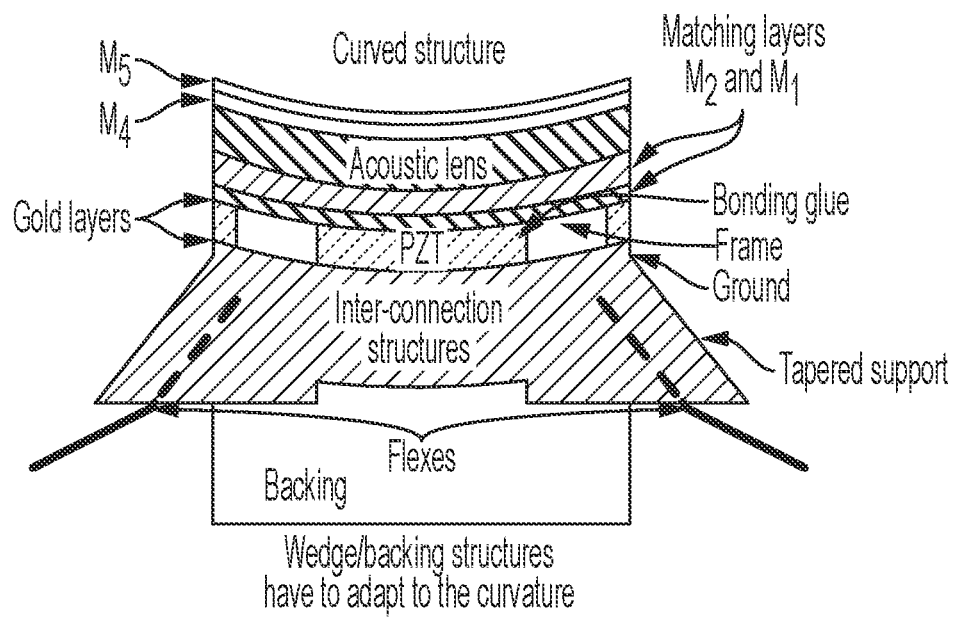
FIG. 15 is a cross-sectional view of a high frequency phased array transducer with a curved transducer stack in accordance with an embodiment of the disclosed technology.

In one embodiment, a curved conductive frame that supports the flex circuits is used as a structural support on the back side of the stack to maintain the desired curvature as shown in FIG. 15. The curved frame can either by applied after the stack is curved or can be applied to the rear element side at the time of molding.

Figure 16:
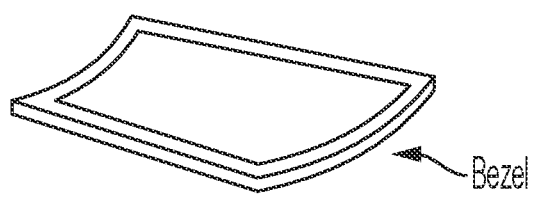
FIG. 16 illustrates a curved bezel that can be used to maintain the curvature of a transducer stack in accordance with an embodiment of the disclosed technology.

FIG. 15 is a cross-sectional view of an ultrasound transducer with a transducer stack that is curved as described. In this embodiment, a support frame is adhered to the back surface of the transducer stack to support flex circuits with traces that connect to the individual transducer elements. In one embodiment, the support frame has a curved shape so that it holds the curved shape of the transducer stack as the stack is pressed against the curved support. In some embodiments, a curved bezel (e.g. a metal of molded ceramic frame) as shown in FIG. 16 may be fixed to the front of the transducer around a perimeter of the lens to help maintain the curvature of the transducer stack.

In another embodiment, a filling epoxy fills the gaps between a curved transducer stack and a flat support frame on the rear surface of the stack. The filling epoxy maintains the curved shape of the stack once it is cured. Once the conductive support frame is secured to the transducer stack, connections between the individual transducer elements and the traces in the flex circuits are made as described above.

From the foregoing, it will be appreciated that specific embodiments of the invention have been described herein for purposes of illustration, but that various modifications may be made without deviating from scope of the invention. For example, the disclosed transducer design can be scaled to operate at lower frequencies (e.g. 2-15 MHz). In addition, aspects of the disclosed technology can be used in more conventional ultrasound transducer designs. Accordingly, the invention is not limited except as by the appended claims.

We claim:

1. An ultrasound transducer, comprising:
   a piezoelectric material having a coefficient of thermal expansion;
   a frame surrounding an outer perimeter of the piezoelectric material, where the frame has a coefficient of thermal expansion that is similar to a coefficient of thermal expansion of the piezoelectric material;
   a filling material placed between the frame and the outer perimeter of the piezoelectric material;
   wherein the piezoelectric material includes a number of kerf cuts that define a number of individual transducer elements;
   a lens secured to the piezoelectric material through one or more matching layers, wherein the frame, piezoelectric material and lens have a concave curvature that is configured to focus ultrasound signals produced from the transducer elements;
   a conductive support frame having a curved shape, wherein the conductive support frame is secured to the piezoelectric material to maintain the concave curvature shape of the piezoelectric material; and
   a curved bezel secured to the front of the lens to maintain the curvature of the lens;
   wherein the lens and the one or more matching layers include filled kerf cuts that are aligned with the kerf cuts in the piezoelectric material.

2. The ultrasound transducer of claim 1, wherein the frame includes a pair of side rails and a filler material surrounding the piezoelectric material such that the filler material can be bent into the concave curvature.

3. The ultrasound transducer of claim 2, wherein the frame is made of alumina.

4. The ultrasound transducer of claim 3, wherein the frame is open on opposing sides and is filled with an epoxy that allows the frame to be bent into the concave curvature.

5. The ultrasound transducer of claim 1, wherein the frame is made of graphite.

6. The ultrasound transducer of claim 1, wherein the frame is made of molybdenum.

7. The ultrasound transducer of claim 1, wherein the curvature in the piezoelectric material is in an elevation direction of the transducer.

8. The ultrasound transducer of claim 1, wherein the curvature in the piezoelectric material is in an azimuthal direction of the transducer.

9. The ultrasound transducer of claim 1, wherein the curvature in the piezoelectric material is in an elevation and azimuthal direction of the transducer.

10. The ultrasound transducer of claim 1, wherein the piezoelectric material has a thickness of 80 microns or less.

11. A phased array ultrasound transducer, comprising:
a piezoelectric material having a coefficient of thermal expansion;
a frame surrounding an outer perimeter of the piezoelectric material, where the frame has a coefficient of thermal expansion that is similar to a coefficient of thermal expansion of the piezoelectric material;
a filling material placed between the frame and the outer perimeter of the piezoelectric material;
wherein the piezoelectric material includes a number of kerf cuts that define a number of individual transducer elements;
a lens secured to the piezoelectric material through one or more matching layers, wherein the lens includes a number of kerf cuts that align with the kerf cuts in the piezoelectric material and wherein the frame, piezoelectric material and lens have a curvature that is configured to focus ultrasound signals produced from the transducer elements;
a conductive support frame having a curved shape, wherein the conductive support frame is secured to the piezoelectric material to maintain the concave curvature shape of the piezoelectric material; and
a curved bezel secured to the front of the lens to maintain the curvature of the lens.

12. The phased array ultrasound transducer of claim 11, wherein the lens includes a number of kerf cuts that align with the kerf cuts in the piezoelectric material that define the individual transducer elements.

13. The phased array ultrasound transducer of claim 11, wherein the frame includes a pair of side rails and a filler material surrounding the piezoelectric material such that the filler material can be bent into the concave curvature.

14. The phased array ultrasound transducer of claim 13, wherein the frame is made of alumina.

15. The phased array ultrasound transducer of claim 14, wherein the frame is open on opposing sides and is filled with an epoxy that allows the frame to be bent into the concave curvature.

16. The phased array ultrasound transducer of claim 11, wherein the curvature in the piezoelectric material is in an elevation direction of the transducer.

17. The phased array ultrasound transducer of claim 11, wherein the curvature in the piezoelectric material is in an azimuthal direction of the transducer.

18. The phased array ultrasound transducer of claim 11, wherein the curvature in the piezoelectric material is in an elevation and azimuthal direction of the transducer.

19. The phased array ultrasound transducer of claim 11, wherein the piezoelectric material has a thickness of 80 microns or less.

* * * * *